United States Patent [19]
Torres

[11] Patent Number: 6,056,951
[45] Date of Patent: May 2, 2000

[54] METHOD OF REDUCING THE CHANCE OF ATTACK OF CELLS IN A BODY BY THE CELLULAR IMMUNE SYSTEM

[76] Inventor: Anthony R. Torres, 79 E. 2050, North Centerville, Utah 84014

[21] Appl. No.: 08/946,606

[22] Filed: Oct. 7, 1997

[51] Int. Cl.[7] .......................... A01N 63/00; A01N 65/00; A01N 1/02; G01N 33/53
[52] U.S. Cl. ........................... 424/93.1; 435/2; 435/7.24; 435/372; 435/378
[58] Field of Search .................................. 435/372, 378, 435/7.24; 424/93.1

[56] References Cited

U.S. PATENT DOCUMENTS

| | | | |
|---|---|---|---|
| 4,473,647 | 9/1984 | Carpenter et al. | 435/240 |
| 4,500,637 | 2/1985 | Neville, Jr. et al. | 435/2 |
| 4,520,226 | 5/1985 | Neville, Jr. et al. | 424/85 |
| 5,047,401 | 9/1991 | Lipsky et al. | 514/19 |
| 5,178,858 | 1/1993 | Reichert et al. | 424/85.8 |
| 5,593,677 | 1/1997 | Reichert et al. | 424/154.1 |
| 5,595,881 | 1/1997 | Kendrick | 435/7.21 |
| 5,759,793 | 6/1998 | Schwartz | 435/7.24 |

OTHER PUBLICATIONS

Kogler, G., et al., High efficiency of a new immunological magnetic cell sorting method for T cell depletion of human bone marrow. 6:163–168, 1990.

"Prevention of Graft–Versus–Host Disease After Bone Marrow Transplantation", Transplantation Proceedings, vol. 27, No. 5 (Oct.), 1995; pp. 2653–2656, by R. Storb.

"Marrow Transplantation from Unrelated Volunteer Donors" by Claudio Anasetti, M.D., et al., Annu. Rev. Med. 1995, 46 169–79.

Warren, R.P., et al. "Direct and Antibody–Dependent Cell–Mediated Cytotoxicity Against HLA Identical Sibling Lymphocytes", Transplantation, vol. 22, No. 6, pp. 631–635, 1976.

*Primary Examiner*—David Saunders
*Assistant Examiner*—Mary Beth Tung
*Attorney, Agent, or Firm*—Mallinckrodt & Mallinckrodt

[57] ABSTRACT

A method of reducing the chance of disease resulting from mononuclear cells in a body attacking desirable cell antigens in the body, such as antigens expressed by normal body cells or desirable engrafted cells, comprises reducing the number of mononuclear cell in the body that are likely to attack such desirable cell antigens. This is done by obtaining cell derived antigens subject to attack by mononuclear cells in the body and also obtaining mononuclear cells to be placed in the body. The mononuclear cells may be from a donor or may be removed from the subject body. The mononuclear cells are reacted, in vitro, with the cell derived antigens, such as by passing the mononuclear cells over a layer of fibroblast cells from the body expressing the desirable antigens, and recovering the mononuclear cells that do not bind to the antigens. These recovered cells are then infused into the body.

18 Claims, 2 Drawing Sheets

METHOD OF REDUCING THE CHANCE OF ATTACK OF CELLS IN A BODY BY THE CELLULAR IMMUNE SYSTEM

BACKGROUND OF THE INVENTION

1. Field

The invention is in the field of immunology, and more specifically, in the field of treating immune systems to reduce the chance of the system attacking beneficial cells. This includes treatments and procedures for reducing the risk of graft versus host disease associated with bone marrow transplantation, diseases associated with organ or other tissue transplants, as well as autoimmune diseases.

2. State of the Art

The cellular immune system in animals, particularly mammals such as human beings, include cells in the blood, such as T-cells, which recognize aberrant cells in the body and attack and destroy such cells. Aberrant cells result, for example, from viral and other infections and cancerous and diseased cells and express one or more abnormal antigens. The aberrant cells are recognized by immune system cells. By recognizing and destroying aberrant cells, a body's cellular immune system kills diseased and other harmful cells and protects the body. However, in some instances (i.e., autoimmune diseases) certain immune system cells attack normal cells. In other instances, such as allogenic bone marrow transplantation, immune system cells attack host cells.

With some cancers, such as leukemia, control of the cancer can only be achieved by treatments such as irradiation or chemotherapy which inadvertently destroy the blood forming cells in the body along with the cancer cells. Bone marrow transplants are done to replace blood forming cells in the body that are destroyed as a result of such treatment. Hematopoietic stem cells are transplanted into the body to form a new immune system. T-cells are part of traditional bone marrow transplants and, since they came from a donor, recognize the host tissue as being foreign, i.e., aberrant, and develop an immune reaction to the antigens on the host cells. This is generally referred to as graft versus host disease (GVHD). Immunosuppressive drugs are used to reduce GVHD. The two main immunosuppressive drugs used over the last two decades are methotrexate and cyclosporin. Although these drugs used alone or in combination decrease the incidence of GVHD, an unacceptable number of patients still die, R. Storb, Transplantation Proceedings, Vol. 27, #5 (October), 1995, pp. 2653–2656. Attempts have been made to prevent GVHD by the removal of T-cells from the donor inoculum with monoclonal antibodies, lectins, or complement lysis so that only stem cells are transplanted. These methods generally reduce the number of T-cells by 1–3 logs and show significant reductions in acute and possibly chronic GVHD. However, since the host is left without a mature cellular immune system for several weeks while the stem cells develop into a new immune system, the success in reducing GVHD is generally associated with an increased risk of infection and relapse of the original malignancy. In addition, secondary tumors such as Epstein-Barr lymphoproliferative disease are likely to appear, C. Anasetti et al., Annu. Rev. Med. 1995, 46:169–179. It is believed that the increased rate of relapse of the original malignancy and possibly the occurrence of secondary tumors is a result of incomplete destruction of the original malignant cells during treatment. The new immune system which develops from the transplant does not recognize the malignant cells as aberrant and thus does not mount an attack. As a result, the few malignant cells that survive treatment are left to grow unchecked by the new immune system. All of these disorders invariably result in death and no improvement in survival rate has yet been realized for patients given T-cell depleted marrow.

With organ or other tissue transplants made into a body having a cellular immune system, the transplant presents foreign tissue to the body. The cellular immune system, recognizing the tissue as made up of foreign or aberrant cells, attacks the transplanted tissue resulting in what is commonly referred to as transplant rejection where the body rejects the transplant. This is also referred to as host versus graft disease (HVGD). Again, in most transplant cases, immunosuppressive drugs are used to inhibit the body's attack on and rejection of the transplant. Since the transplant was probably necessary to save the recipient's life, rejection of the transplant usually results in death. However, use of immunosuppressive drugs to prevent rejection of the transplant generally reduces the ability of the immune system to attack unwanted disease or other harmful cells so the risk of death from disease and infection is increased.

With autoimmune diseases, such as multiple sclerosis, something abnormal happens to a body's cellular immune system and the immune system attacks and destroys the body's own cells. This generally results in death unless the immune system's attack on the body can be controlled. Often, such attacks can be controlled by use of immunosuppressive drugs, however, the success of such control depends upon the disease and the individual. Also, as indicated, use of immunosuppressive drugs reduces the body's ability to fight disease and infection.

SUMMARY OF THE INVENTION

According to the invention, the risk of disease resulting from mononuclear cells in a body attacking normal or grafted cellular antigens (desirable cellular antigens) in the body, such as graft versus host disease (GVHD) or host versus graft disease (HVGD), or some autoimmune diseases, can be significantly decreased by reducing the number of mononuclear cells in the blood in the body that show a tendency to attack the normal or grafted cells. This is done by removing such cells by obtaining cellular antigens from normal or grafted cells likely to be attacked in the body and reacting, in vitro, mononuclear cells to be infused into the body with such normal or grafted cellular antigens. The cytotoxic mononuclear cells, i.e., the cells that would tend to attack such antigens in the body, bind to these cellular antigens. The cells that do not bind to the antigens, i.e., the cells that generally will not attack cells in the body having such antigens, are recovered and infused into the body. The mononuclear cells may be obtained from a donor with the recovered cells being injected into the body of a host, or the mononuclear cells may be withdrawn from the body such as by withdrawing blood from the body, reacted with the antigens, and then infused back into the body. When extracted and reinfused into the body, the procedure can be done in a manner to treat substantially the entire body's blood supply.

In connection with bone marrow transplants, the risk of graft versus host disease and the chance of infection and relapse of malignancy or secondary tumors can be reduced by a combination of depleting the T-cells in the transplant inoculum and infusing selected donor T-cells into the host to replace the depleted T-cells but reduce the number of T-cells that tend to cause GVHD. The selected and infused donor T-cells boost and maintain the host's immune system while the host's hematopoietic system develops from the graft and provide continuing protection against relapse of the original malignancy. The T-cells for infusion into the host are selected by the selective removal from donor mononuclear cells, such as donor peripheral blood cells, of cytotoxic T-cells, such as $CD8^+$ cells, which attack normal host tissue. The cytotoxic T-cells which attack tumor cells and virally or otherwise infected cells remain and can be amplified in number before infusion into the host. The selective removal is accomplished by incubating the donor mononuclear cells with cell derived antigens from the host that are recognized by donor T-cells included in the donor mononuclear cells and recovering the cells that do not attach to the antigens. In a preferred embodiment of the invention the antigens are provided by host fibroblast cells attached in a monolayer to a substrate. The donor cells are passed over the host fibroblasts and the mononuclear cells that do not adhere to the fibroblast are recovered. The selective removal step, sometimes referred to herein as panning, may be repeated several times, with the recovered cells amplified in number each time, if desired, until only a small percentage of cells adhere to the fibroblast. These selected cells are then amplified in number and infused into the host.

If desired to increase the cellular activity in infused cells against the original malignancy in the host, the mononuclear cells from the donor may be activated against the original malignancy in the host prior to selection. This activation step involves culturing the donor mononuclear cells with cell derived antigens from malignant cells from the host. Since the malignant cells also have the body's normal antigens, the activation step will result in increased numbers of both cells which tend to attack the normal body cells as well as cells which tend to attack the original malignancy. However, the selection or panning step reduces the number of cells which attack the normal cells while leaving the increased number of cells to attack the original malignancy. If this is done, the selection not only reduces the T-cells likely to cause GVHD but also concentrates the T-cells likely to prevent malignancy relapse.

While it is currently preferred with bone marrow transplants to treat blood cells from the donor and then infuse such cells into the host in coordination with the bone marrow transplant using T-cell depleted inoculum, a host's blood can be treated after the transplant, possibly waiting until signs of GVHD appear. In such cases, host fibroblast cells are obtained from the host either before or after treatment and attached to a substrate. The host's blood is drawn continuously and the white blood cells separated as in leukophoresis, and the blood returned to the body. This would continue for a period of time to separate substantially all white cells from the blood in the body. The separated white cells are selected or panned by passing them over the fibroblast cells and those that pass over the fibroblast cells are infused back into the body. In this way, the cells causing the GVHD in the body are removed from the body to substantially lessen the chance of GVHD while the remaining cells which attack disease, infection, and the original malignant cells are returned to the body to maintain its immune system and fight relapse of the original malignancy.

Treatment of hosts receiving organ or other tissue transplants would be similar to treatment of a bone marrow transplant host after the transplant takes place in that the blood of the host is withdrawn on a continuing circulation basis with white cells separated therefrom. These white cells are passed over fibroblast cells obtained from the organ or other tissue transplanted into the host or to be transplanted into the host. The cells that pass over such fibroblasts are infused back into the body. In this way, the host cells likely to attack the foreign engrafted tissue are removed from the host, leaving the host with cells to attack other foreign tissue or abnormal cells in normal manner to prevent disease and infection.

Treatment of bodies suffering autoimmune diseases would be similar using normal cells, e.g., fibroblasts, from the body to remove the lympocytes likely to attack such normal tissue.

THE DRAWINGS

The best mode presently contemplated for carrying out the invention is illustrated in the accompanying drawings, in which:

FIG. 1 is a graph showing cytotoxicity of cytotoxic T lymphocytes against $^{51}Cr$ labeled fibroblasts and chronic myeloid leukemia cells after activation and before and after selection of the T-cells;

FIG. 2, a graph showing cytotoxicity of activated, selected cytotoxic T lymphocytes five days after selection and of non-activated donor peripheral blood lymphocytes against $^{51}Cr$ labeled fibroblasts and chronic myeloid leukemia;

FIG. 3, a graph showing cytotoxicity of cytotoxic T lymphocytes against chronic myeloid leukemia cells from the host and from two other individuals; and FIG. 4, a graph showing cytotoxicity of cytotoxic T lymphocytes from a bone marrow transplant host suffering from graft versus host disease.

DETAILED DESCRIPTION OF THE ILLUSTRATED EMBODIMENT

Figure 1:
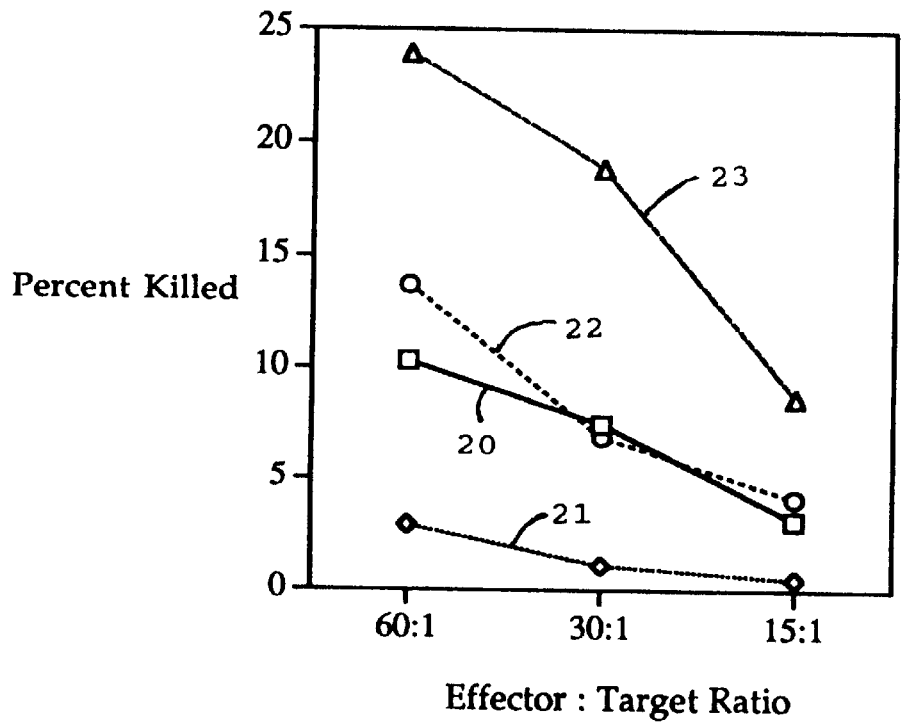

There are several situations where mononuclear cells comprising part of a body's cellular immune system undesirably attack other body cells. In the case of autoimmune diseases, a body's mononuclear cells begins to attack normal body cells. In organ and other tissue transplants, the body's mononuclear cells correctly recognize the transplanted or grafted tissue as foreign or aberrant tissue and attack it. This is referred to as host versus graft disease (HVGD). However, in such cases it is undesirable for the body's immune system to attack such foreign tissue. In the case of bone marrow transplants, a foreign immune system may be transplanted into a body which then recognizes the normal body cells as foreign or aberrant and attacks such cells. This is referred to as graft versus host disease. Reducing the risk of such attacks in any of these situations in accordance with the invention are similar in that the mononuclear cells likely to attack the normal or engrafted cells (desirable cells) in the body are substantially removed from the body. The invention will be described in detail in connection with reducing the chance of GVHD in bone marrow transplant situations.

Cell therapy has been an established technique since the 1970's with the advent of Bone Marrow Transplantation (BMT). Bone marrow transplanted from one's self is an autograft and bone marrow transplanted from other individuals is called an allograft. BMT is a proven technique that is used for many indications including aplastic anemia and leukemia. Although standard transplants use actual bone marrow tissue extracted from the donor, modern procedures now use bone marrow stem cells taken from a donor's blood. This has been made possible by the advent of recombinant granulocyte macrophage colony stimulating factors (GM-CSF) which are infused into the donor to enrich the donor's blood with stem cells which will seed the recipient's or host's bone marrow and differentiate into the different blood cell types. These potent cytokines cause a margination of stem cells into the vasculature (blood stream) of the donor which are collected by a standard blood bank procedure (leukophoresis). These stem cells along with other white cells, such as T-cells, are separated from the donor's blood to form the inoculum which is infused into the donor as the transplant. Graft versus host disease (GVHD) is the major medical complication of BMT followed by infections with bacteria, fungi, and virus especially cytomegalovirus (CMV).

GVHD is an immune reaction of donor cytotoxic T-lympocytes contained in the transplant inoculum against histoincompatible antigens on normal recipient tissue. GVHD may involve the host's skin, oral mucosa, eyes, liver, and/or lungs, and despite treatment with immunosuppressive therapy, kills a significant number of transplant patients. Death is often caused by infections and is twice as likely to occur among patients with acute GVHD compared to mild or no GVHD. Means to decrease the death rate from GVHD involve evaluating risk factors such as HLA-matching, age, sex, child birth and lowering the chances of infection by decontamination and laminar-air flow room isolation.

Different routes have been taken to reduce the chances of GVHD: the administration of immunosuppressive drugs following the transplant is commonly done.

Graft versus host disease (GVHD) in connection with bone marrow transplants or other lymphocyte or mononuclear cell transfers from a donor to a host (also sometimes referred to as a patient or recipient) occurs when cytotoxic T-cells such as CD8+ cells in the donor peripheral blood mononuclear cells (PBMC) which are infused or transplanted into the host attack host cells that are antigenic. The prior art has found that the risk of GVHD can be reduced by depleting the transplant inoculum of T-cells. However, while this reduces the occurrence of GVHD, the incidence of infection increases and the incidence of original malignancy relapse increases. As indicated, the overall death rate is not reduced by T-cell depletion. The present invention couples the depletion of T-cells in the transplant inoculum with the separate infusion of selected T-cells which maintain and even increase the host's ability to fight infections and to fight the original malignancy. The T-cells are selected to reduce the number of cytotoxic T-cells that attack host cells while still providing the host with T-cells to fight infection and malignancies.

The T-cells for infusion into the host are selected by mixing donor mononuclear cells with host cell derived antigens recognized by the donor T-cells. The mononuclear cells that are antigen-specific, i.e., attach to the host antigens, attach to and are retained by such host antigens while the other donor cells are recovered from the mixture. This procedure may be performed several times if considered necessary to reduce the number of cytotoxic T-cells in the mononuclear cells to be infused. A lesser percentage of the number of donor T-cells attaching to the antigens each time. The recovered cells are generally amplified in number for infusion into the host. With the depletion of antigen specific cells and the enhancement of the non-antigen specific cells, the risk of GVHD from the infused cells is substantially reduced while the infused cells provide the host with protection against infection and relapse of malignancies.

The normal procedure for bone marrow stem cell transplants is to initially select the donor. Donors are carefully selected to reduce the risk of GVHD disease by HLA-matching between donor and host, and by further matching such factors as age, sex and child birth. However, while risk of GVHD can be reduced by such matching, it has not been possible to eliminate such risk and substantial risk still exists with even the best host and donor matching.

The need for a bone marrow stem cell transplant arises because the only treatment that appears to have a chance of killing the disease in the host also kills the host's cellular immune system. Thus, the patient or host is treated to kill the target disease, and as a result of such treatment, the host's cellular immune system is also killed. Common methods of treatment include radiation treatment and chemotherapy, either alone or together, with or without accompanying surgery. After such treatment, it is necessary to provide the patient with a means for regenerating the patient's immune system. The bone marrow or bone marrow stem cell transplant provides the basis for this immune system regeneration. The donor is treated to enrich his or her blood with bone marrow stem cells. The donor's blood is drawn and is centrifuged to separate the white blood cells which include the desired stem cells necessary to regenerate the host's immune system from the rest of the blood. The separated white blood cells will also include the donor's T-cells. The separated white blood cells form the transplant inoculum that is infused into the host. After infusion into the host, the infused or transplanted stem cells will seed the host's bone marrow and will differentiate into different blood cell types. This regeneration of the immune system, i.e., the production by the host of T-cells which can attack aberrant cells, such as infected cells, takes several weeks to several months.

As indicated, a current procedure to reduce the risk of GVHD is to deplete the donor's T-cells in the inoculum prior to infusion of the inoculum into the host. However, depletion of the T-cells in the inoculum leaves the host without cellular immunity to infection until the infused stem cells create a new hematopoietic system in the host. Without T-cells during this regeneration time, many patients die from infection. In addition, many of these patients die of relapse of the original malignancy, even after regeneration of their immune system. If any of the original malignant cells survive the treatment to kill such cells, which is common with current treatment which may not be as effective as desired, the inventor believes that such cells may be recognized as self by the new hematopoietic system and the new T-cells produced by the host do not attack such malignant cells. This would allow relapse of the original malignancy in the host.

In the currently preferred practice of the invention, prior to the treatment of the host to kill the disease, fibroblasts or other material from which cell antigens can be derived are obtained from the host. It is preferred that malignant cells with antigens also be obtained from the host. Also, blood from the donor is obtained. Peripheral blood mononuclear cells (PBMC) are separated from the donor's blood. While the PBMC from the donor could then go through the selection step, it is presently preferred that the T-cells in the donor PBMC be activated by culturing the PBMC with malignant cells from the host. This causes the cells specific to the malignant cell's antigen to multiply. Also, however, since these cells contain normal antigens as well as the disease antigens, T-cells specific to the host antigens also are activated and multiply. In the activation step, the PBMC and host malignant cells are cultivated for a time generally sufficient for the antigen specific cells to multiply to the desired degree. After the activation step, the activated PBMC go through the selection or panning step. The activated PBMC are mixed with the host's normal cell derived antigens (malignant cell antigens are not included). It is presently preferred that these cell derived antigens be provided in the form of host fibroblast cells, particularly in the form of a monolayer of fibroblast cells attached to a substrate. The donor's cells may be amplified in number in culture if necessary or desired prior to the mixing to increase the number of donor cells available. In the mixing of the donor cells with host cell derived antigens, donor T-cells which would attack the host cells, i.e., host antigen specific cells which attach to the host antigens, attach to the fibroblasts. The cells that do not attach to the fibroblasts are recovered from the mixture. These non-attaching cells are cells least likely to attack the host. It is presently preferred to attach the host fibroblasts to a substrate and pass the donor mononuclear cells over the substrate. The nonattached cells are then merely washed from the substrate. It is presently preferred with activated cells to repeat this step several times until the number of donor cells attaching to the fibroblasts is a relatively small percentage, such as less than 10%. If desired, the number of recovered cells can be amplified in number after each pass. This amplification tends to concentrate and increase the number of mononuclear cells which do not cause GVHD. In one test, 75% of the host T-cells attached to and remained with the fibroblasts on the first pass, 39% of the remaining T-cells on the second pass, 16% on the third pass, and 6% on the fourth pass. After the fourth pass, it was determined that the donor T-cells were sufficiently purified by removal of the antigen specific cells for use as selected T-cells.

The T-cells remaining after the desired number of selection or panning passes may be amplified in number by cell culture techniques and are ready for infusion into the host. Such infusion will take place after treatment of the patient and may take place substantially simultaneously with, before or immediately after the transplant inoculum infusion. These infused selected T-cells provide an immediate immune system for the host to fight infection and cancer or other aberrant cells. However, because most of the donor T-cells which would have a tendency to attack the host have been removed, the chance of GVHD is substantially reduced. Further, these infused T-cells may remain in the host's body for many years. Because the original malignancy that was treated will be recognized by many of these infused T-cells as aberrant, these T-cells will attack such malignant cells thereby substantially reducing the risk of malignancy relapse.

EXAMPLE

Primary Cell Culture and Cytotoxic T Lymphocyte Generation

A standard Histopaque gradient technique was used to isolate peripheral blood mononuclear cells (PBMC) from a donor's whole blood. Chronic myeloid leukemia cells (CML) were obtained from the prospective host. These CML cells were treated with mitomycin C to prevent cell division and reduce the chance of their contaminating other cell cultures. Some of these CML cells were frozen and placed in cryostorage. Punch biopsy fibroblasts were also obtained from the prospective host and were established in culture in DMEM+10% FBS+gentamycin.

One $\times 10^6$ donor PBMC were mixed with $1 \times 10^6$ mitomycin C-treated CML cells from the prospective host and placed in 24 well tissue culture plates. Culture medium was lymphocyte culture fluid (LCF) from Selective Cell Therapies, Inc., Salt Lake City, Utah, supplemented with gentamycin and 100 U/ml IL-2. This treatment activates the T-cells of PBMC against the normal cell antigens and the leukemia cell antigens so they become cytotoxic T lymphocytes (CTL). After seven days in culture the CTL ($3 \times 10^6$) were washed and added to a confluent (T-25 flask) monolayer of fibroblasts in 10 ml culture medium and allowed to incubate for 15 minutes at 37° C. The monolayer of fibroblasts had been treated with mitomycin C to prevent further growth of such cells. The non-adhering CTL cells were washed from the fibroblasts and returned to 24-well plates for further expansion. These non-adhering CTL cells were expanded and exposed to fibroblasts three additional times, once every three days, before testing for cytotoxic activity in a chromium release assay. The exposure to the fibroblasts is referred to as the selection or panning step and constitute panning of the CTL. In some cases the PBMC are panned where PBMC are exposed to the fibroblasts without the activation step described.

Flow Cytometry

Fluorescence labeled antibodies specific for CD3 (T lymphocytes), CD4 (T inflammatory and helper lymphocytes), CD8 (T cytotoxic lymphocytes), CD56 (natural killer cells) and HLA-DR (activated T lymphocytes) were used to characterize the CTL periodically during culture. Analysis was done on an EPICS C flow cytometer. This periodic labeling showed that the population of CD8+ cells increased during the culture time.

Cytotoxicity Assay

A standard four hour chromium release assay was carried out with the CTL. The assay is described in Warren, et al., Transplantation, Vol. 22, No. 6 (December) 1976, pp. 631–635, incorporated herein by reference. Frozen CML target cells were thawed, and incubated at 37° C. for one hour prior to labeling with 51-chromium ($^{51}$Cr). Target fibroblast cells were prepared in single cell suspension by treating with trypsin-EDTA and washed prior to labeling with $^{51}$Cr.

Results

After seven day incubation of donor PBL with mitomycin C-treated CML lymphocytes the resulting CTL were incubated for fifteen minutes with fibroblasts in T-25 culture flasks (panning) four times at three day intervals as indicated. The cell numbers before each incubation and the cell numbers washed from the fibroblasts (the number of cells recovered or panned after each incubation) were as follows:

| Panning | Before | After | Percent Loss |
|---------|--------|-------|--------------|
| 1 | $3 \times 10^6$ | $0.75 \times 10^6$ | 75 |
| 2 | $1.7 \times 10^6$ | $1.05 \times 10^6$ | 39 |
| 3 | $2.79 \times 10^6$ | $2.35 \times 10^6$ | 16 |
| 4 | $5.2 \times 10^6$ | $4.9 \times 10^6$ | 6 |

The greatest loss of CTL occurred during the first panning exposure to fibroblasts. Here 75% of the CTL were bound to the fibroblasts and remained in the flask. Later pannings resulted in progressively fewer CTL removed. This shows that the cells expected to attack the fibroblasts, i.e., the cells which would cause GVHD, are actually being removed from the CTL by the pannings. Following removal of the CTL by incubation with fibroblasts, the CTL were maintained in culture with IL-2 and mitomycin C-treated CML cells as stimulators.

FIG. 1 shows the cytotoxic activity of CTL cells prepared as described above at various effector:target ratios before and after panning. Line 20 shows the percentage of host fibroblast cells lysed or killed by the donor CTL cells after seven days in primary culture with CML cells but before panning, i.e., without selection. Line 21 shows the percentage of host fibroblast cells lysed or killed by the donor CTL cells after selection by the four pannings indicated. FIG. 1 shows a significant drop in the number of fibroblast cells killed at all effector:target ratios indicating that a significant number of T-cells that attack the fibroblast are removed by the pannings. The removed cells are those that are likely to cause GVHD. Line 22 shows the host CML cells killed by the donor CTL cells without selection while line 23 shows the host CML cells killed by the donor CTL cells after selection. FIG. 1 shows a very significant increase in the CML cells killed by the selected cells as opposed to the CTL cells prior to selection indicating that the selected cells are much more active against the cancer cells. In the chromium release tests performed, a 25% lysis is very significant. Thus, the results of FIG. 1 show panning CTL on fibroblasts increased the cytotoxicity against $^{51}$Cr labeled CML targets while it decreased the cytotoxicity against $^{51}$Cr labeled fibroblasts. Prior to panning, the level of cytotoxicity against fibroblasts and CML cells was similar.

Figure 2:
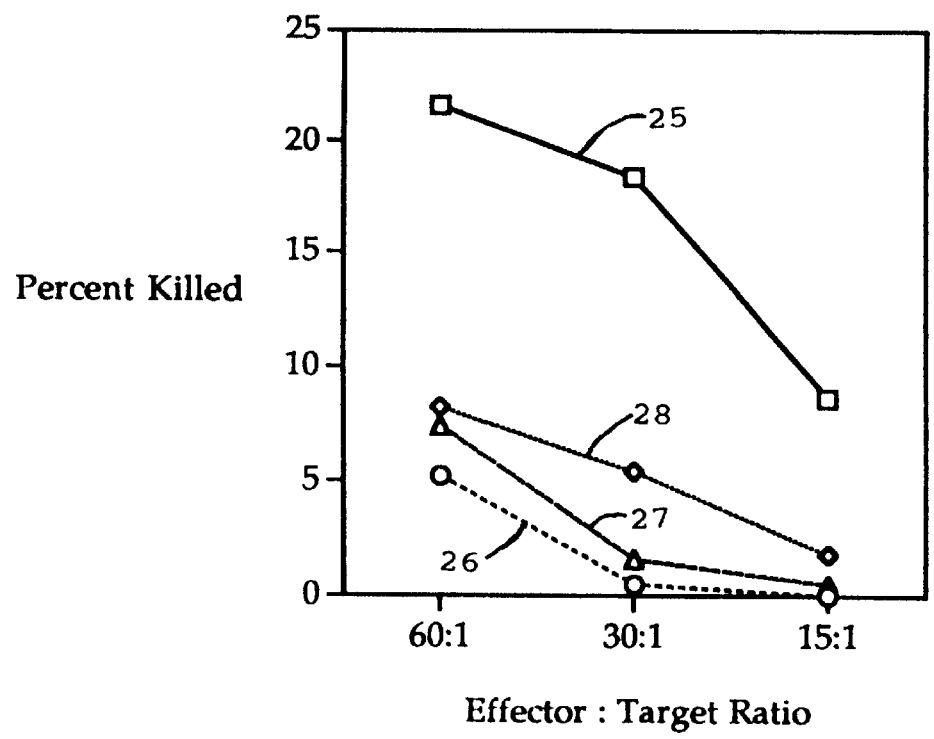

Following the four pannings, some of the cells were cultured for an additional five days and again tested for cytotoxicity against CML and fibroblast targets in a chromium release assay. The results are shown in FIG. 2. Line 25 shows that after the five days in culture, the CTL cells remained very effective in killing CML cells with only a small decrease in effectiveness from that shown in FIG. 1. Line 26 shows that the decreased specificity for fibroblasts also remained with only a small increase in killing of fibroblasts at the high effector target ratio. FIG. 2 also shows the lysis of CML and fibroblasts using the donor PBMC, i.e., the blood cells without activation by being cultured with CML or other host cells. Line 27 shows the percent of host fibroblasts killed by the donor PBMC. As expected, comparison with line 22 of FIG. 1 shows less killing of the fibroblasts by the unactivated PBMC than by the activated CTL. The significance of line 27, however, is that the killing of fibroblasts by the panned CTL as shown by line 26 in FIG. 2, and by line 21 in FIG. 1, is well below the line 27 in FIG. 2 indicating that the panned CTL (activated PBL) kill fewer fibroblast cells than the PBMC. This indicates that the panning significantly decreases the cells that are believed to cause GVHD. Line 28 shows that the killing action of the unactivated donor PBMC cells is less than the activated and panned CTL against CML cells, (compare with line 25, FIG. 2 and 23, FIG. 1).

Flow cytometric analysis of the cultured CTL after panning on fibroblasts is:

| Days in | Percent | | | |
| --- | --- | --- | --- | --- |
| Culture | CD3+CD4+ | CD3+CD8+ | CD56+ | CD3+HLA-DR+ |
| 1 | 22 | 79 | 3 | 56 |
| 6 | 5 | 93 | 0 | 72 |
| 15 | 0 | 98 | 0 | 68 |

The majority of the CTL are CD3+CD8+ indicating that they are cytotoxic T lymphocytes. A few CD56+ (natural killer cells) were present at day one but were not detected later on. Some CD3+CD4+ cells continued to proliferate in the cultures but by day fifteen were undetectable. The high percentage of HLA-DR+ cells indicates activated cells in the cultures.

Figure 3:
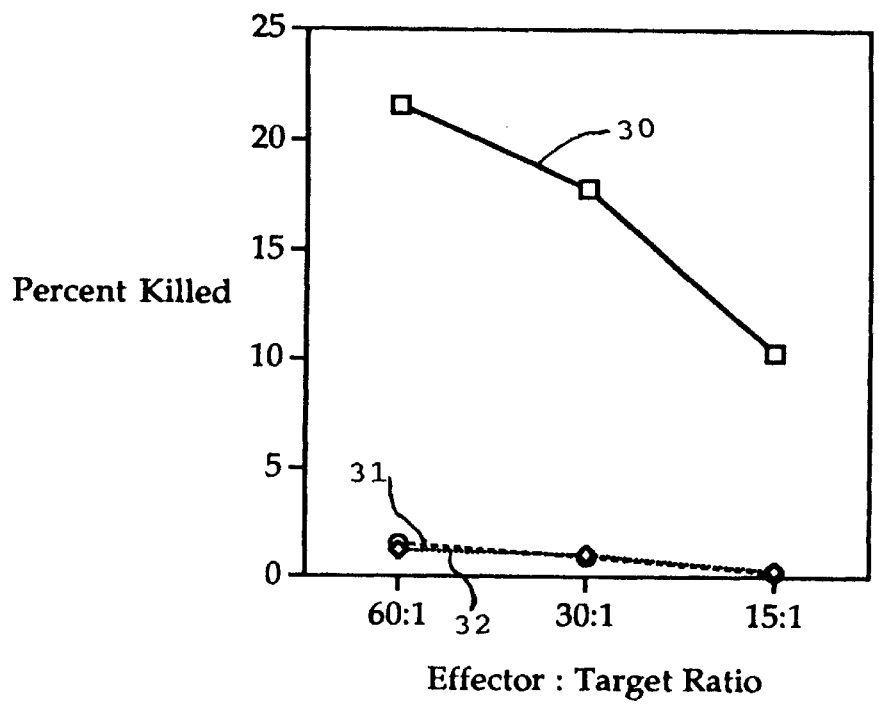

FIG. 3 shows the cytotoxic activity of the donor CTL against the prospective host CML, line 30, and against two unrelated individuals with CML, lines 31 and 32. It is apparent from this data that the CTL generated from the donor PBMC against the recipient CML cells are specific for those cells and do not lyse CML cells from other individuals. These results are consistent with the well established principle that cytotoxicity by CTL cells are HLA-restricted, i.e., require recognition of self HLA molecules in order to generate a cytotoxic response against CML-specific antigens. The host HLA recognition factor is developed in the donor CTL by the incubation with host CML cells (activation).

This example provides evidence that the panning of PBMC or CTL is very effective in removing cells that have a tendency to attack the body's normal cells, thus significantly reducing the chance of GVHD. It also provides evidence that in cases of CML requiring bone marrow transplantation, CTL with a highly specific cytotoxic activity against the host's leukemic lymphocytes can be generated in vitro from donor PBL. These cells can be expanded in tissue culture using culture methods that maintain the activated CTL for extended periods. The panning which reduces the number of cells likely to cause GVHD results in a higher concentration of CML specific CTL and provides a useful method for generating a large number of CML specific CTL in a short period of time. Once generated, the CTL appear to be specific for the stimulator CML cells and are not effective in lysing CML cells from other individuals.

In the described procedure, fibroblasts were grown to a monolayer and then treated with mitomycin C to inhibit their continued ability to divide. Other cells, in addition to fibroblasts, either living or irradiated, can also be used. In addition, cell membranes or fragments of membranes can be used. Even cell surface antigens can be extracted and used in solution or with solid supports.

Figure 4:
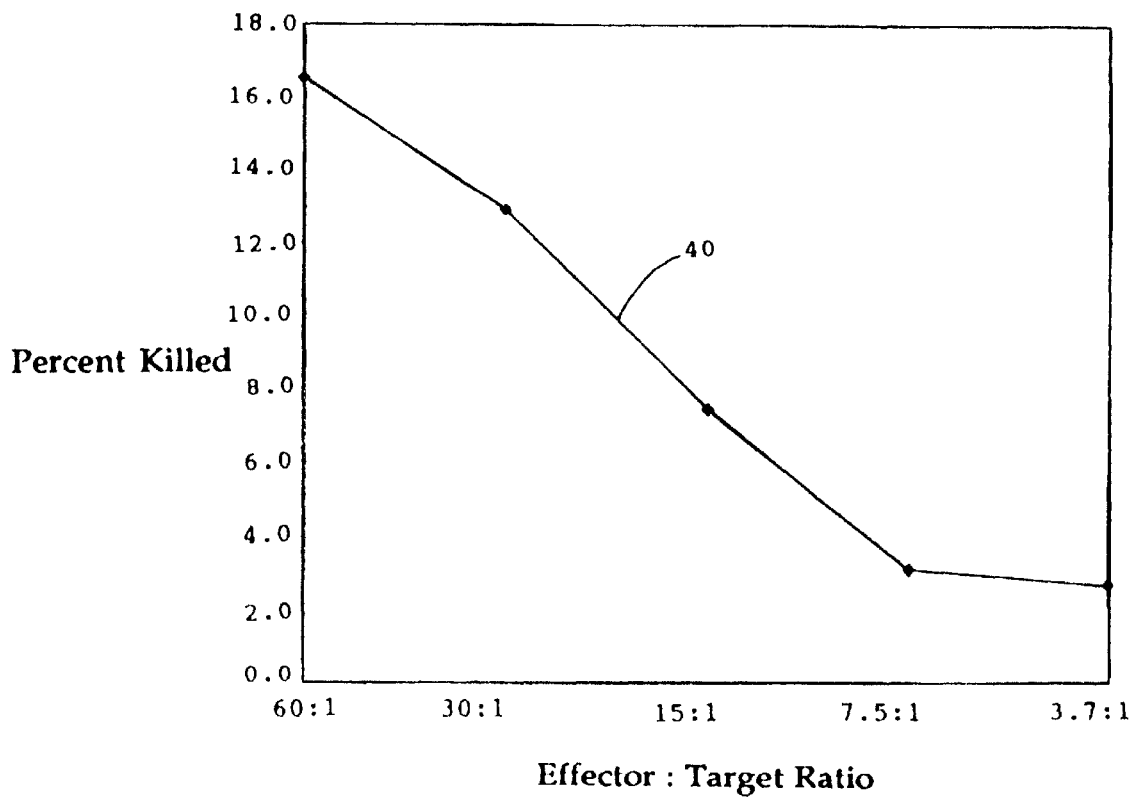

FIG. 4 shows the cytotoxic activity of engrafted PBMC against normal host or recipient fibroblasts. The bone marrow transplant was performed in normal manner without depletion of T-cells in the transplant inoculum. The engrafted PBMC were drawn from the host six months after the transplant. At the time the engrafted PBMC were taken from the host, the host was suffering from severe GVHD despite being HLA identical with the donor. Line 40 shows the percent of normal host fibroblast cells killed by the engrafted PBMC. This percentage is 16% at the 60:1 E:T ratio and drops to about 7% at the 15:1E:T ratio. This is a relatively high kill rate for this test. Lines 21, FIG. 1, and 26, FIG. 2, show significantly lower kill rates, i.e., about 3% and 5%, respectively, compared to the 16%, indicating that the kill rates after the panning are substantially below those indicated for severe GVHD. This indicates that the lower levels of cytotoxicity obtained after panning as indicated in FIGS. 1–3 is effective in reducing the chance of GVHD.

Where a host has received a transplant and developed GVHD as did the host whose blood was drawn and tested for FIG. 4, the method of the invention can be used for treatment by withdrawing the blood from the host, preferably on a continuous circulation basis, treating such blood, and returning the treated blood to the host. While the blood itself could be "panned", e.g., passed over the layer of fibroblasts and then returned to the body, the white blood cells can be removed from the blood withdrawn from the body and the blood, minus the white cells, returned to the body. The separated white cells are then panned and the cells that do not stick to the fibroblasts returned to the body. Several pannings could be performed before returning the white cells to the body. In this way, the T-cells in the body that attack the normal cells and cause GVHD are removed from the blood stream. Several treatment sessions may be necessary to reduce the number of selected T-cells to levels that would reduce the GVHD.

In the case of organ or other tissue transplants, the method of the invention can be used either in preparation for the transplant or after the transplant. For such treatment, fibroblast cells or other normal cell antigens of the tissue to be transplanted or tissue that has been transplanted are obtained and used as the cells or antigens for panning. The blood from the host is withdrawn on a continuous basis and either panned directly or the white cells removed such as by leukophoresis and panned. In this manner, the T-cells from the host's blood that would tend to attack the transplant tissue are removed. As indicated, such cells could be removed from the host prior to the transplant, or after the transplant.

Treatment of autoimmune diseases would be similar where white blood cells of the patient are removed as described above. Panning would take place using normal cells or cell antigens from the patient. In this way, T-cells likely to attack the patient's normal cells are removed.

While the antigens for the panning step have been described as fibroblast cells attached to a substrate, such antigens may be provided by other means such as cell fragments or solubilizing the antigens with or without support.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

What is claimed is:

1. A method of reducing the chance of disease resulting from mononuclear cells in a body attacking desirable cell antigens in the body, comprising the steps of:

obtaining desirable cell derived antigens subject to attack by mononuclear cells in the body;

obtaining mononuclear cells to be placed in the body;

reacting the mononuclear cells with the cell derived antigens;

recovering the mononuclear cells that do not attach to the antigens; and infusing the recovered cells into the body.

2. A method according to claim 1, wherein the cell derived antigens are bound to a substrate, the step of reacting mononuclear cells with the antigens includes passing the mononuclear cells over the substrate with bound antigens, and the step of recovering the mononuclear cells that do not attach to the antigens includes the step of collecting the cells that pass over the substrate without attaching thereto.

3. A method according to claim 2, wherein the steps of passing the mononuclear cells over the substrate with bound antigens and collecting the cells that pass over the substrate without attaching thereto form a set of steps and are repeated at least once using for the repeated steps the cells that were collected during the previous set of steps.

4. A method according to claim 3, including the additional step of amplifying in number the collected cells prior to repeating the set of steps.

5. A method according to claim 4, additionally including the step of amplifying in number the collected cells prior to infusing the collected cells into the body.

6. A method according to claim 1, additionally including the step of amplifying in number the recovered cells prior to infusing the recovered cells into the host.

7. A method according to claim 1, wherein the steps of reacting the mononuclear cells with the cell derived antigens and recovering the mononuclear cells that do not attach to the antigens form a set of steps and are repeated at least once using for the repeated steps the cells that were recovered during the previous set of steps.

8. A method according to claim 7, including the additional step of amplifying in number the recovered cells prior to repeating the set of steps.

9. A method according to claim 1, wherein the disease is graft versus host disease likely to result from a bone marrow transplant to a host who has been treated with the result of such treatment being substantial killing of the host's cellular immune system and with the transplant from a donor from whom stem cells have been removed for infusion into the host as the transplant after treatment of the host, wherein the cell derived antigens are cell derived antigens from the host and include normal cell antigens from the host, the mononuclear cells are cells taken from the donor, and the infusion into the body of the cells that do not attach to the antigens is infusion of such cells into the host which takes place in coordination with the transplant.

10. A method according to claim 1, wherein the disease is graft versus host disease in a host having received a bone marrow transplant from a donor from whom stem cells have been removed and infused into the host as the transplant after treatment of the host where such treatment has resulted in substantial killing of the host's cellular immune system, wherein the cell derived antigens are cell derived antigens from the host and include normal cell antigens from the host, and the mononuclear cells are cells taken from the host after the transplant which include donor origin mononuclear cells.

11. A method according to claim 1, wherein the disease is host versus graft disease likely to result from a transplant received by a host, wherein the cell derived antigens include cell derived antigens of donor origin present in the transplant tissue, and the mononuclear cells are cells taken from the host.

12. A method according to claim 11, wherein the mononuclear cells are taken from the host prior to the transplant.

13. A method according to claim 12, wherein the cell derived antigens are cell derived antigens taken from the transplant tissue prior to performing the transplant.

14. A method according to claim 11, wherein the mononuclear cells are taken from the host and infused into the host after the transplant.

15. A method of reducing the chance of graft versus host disease in a patient host treated for a malignancy and receiving a bone marrow transplant from a donor and for reducing the chance of infection and relapse of the malignancy, comprising the steps of:

obtaining for cellular selection mononuclear cells containing T-cells from the donor;

obtaining, from the host, normal cell derived antigens recognized by T-cells included in the donor mononuclear cells;

incubating the mononuclear cells from the donor with the host antigens and recovering the donor mononuclear cells that do not attach to the host antigens;

infusing the recovered cells into the host; and in coordination with infusing the recovered cells into the host, infusing into the host inoculum from the donor which constitutes the bone marrow transplant after substantial depletion of T-cells from the inoculum.

16. A method according to claim 15, additionally including the step of amplifying in number the recovered cells prior to infusing the recovered cells into the host.

17. A method according to claim 15, wherein the T-cells in the donor mononuclear cells are activated against the malignancy prior to the step of incubating the cells with the host antigens.

18. A method according to claim 17, wherein the activation of the T-cells includes the step of culturing the donor mononuclear cells with antigens expressed by malignant host cells.

* * * * *